(12) United States Patent
Ueoka et al.

(10) Patent No.: US 6,528,692 B2
(45) Date of Patent: Mar. 4, 2003

(54) PROCESS FOR PRODUCING BROMO-AROMATIC CONDENSED RING COMPOUND

(75) Inventors: Takahiro Ueoka, Tsukuba; Hideyuki Ikehira, Mukou, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/021,071

(22) Filed: Dec. 19, 2001

(65) Prior Publication Data
US 2002/0137975 A1 Sep. 26, 2002

(30) Foreign Application Priority Data
Dec. 27, 2000 (JP) ........................................ 2000-398553

(51) Int. Cl.$^7$ ................................................ C07C 17/00
(52) U.S. Cl. .................... 570/201; 570/190; 570/206
(58) Field of Search ................................ 570/190, 201, 570/206

(56) References Cited

U.S. PATENT DOCUMENTS 4,990,705 A * 2/1991 Nonn

FOREIGN PATENT DOCUMENTS

| JP | 1-238546 A | 9/1989 |
| JP | 10-289786 A | 10/1998 |

OTHER PUBLICATIONS

*Organic Syntheses*, Collective vol. 4, A Revised Edition of Annual vols. 30–39, Norman Rabjohn, *Editor–in–Chief*, John Wiley & Sons, Inc., Dec., 1962, pp. 947–950.
*Organic Syntheses*, Collective vol. 1, A Revised Edition of Annual vols. I–IX, Henry Gilman, *Editor–in–Chief*, John Wiley & Sons, Inc., Seventh Printing, Jan., 1956, pp. 207–209.
C. P. Keszthelyi et al., "Electrogenerated Chemiluminescence. XIX. Preparation and Chemiluminescence of 5, 12–Dibromo–5,12–dihydro–5, 6,11,12–tetraphenylnaphthacene", *Journal of Organic Chemistry*, vol. 39, No. 19, 1974, pp. 2936–2937.

* cited by examiner

*Primary Examiner*—Alan Siegel
(74) *Attorney, Agent, or Firm*—Sughrue Mion, PLLC

(57) ABSTRACT

Provided is a process for producing a bromo-aromatic condensed ring compound which comprises reacting an aromatic condensed ring compound in which the number of carbon atom constituting the aromatic condensed ring is 15 or more with a N-bromo carboxylic acid amide in the presence of a chlorinated hydrocarbon compound and sulfuric acid to brominate said aromatic condensed ring compound.

4 Claims, No Drawings

PROCESS FOR PRODUCING BROMO-AROMATIC CONDENSED RING COMPOUND

BACKGROUND OF THE INVENTION

1. Field of the Invention

The present invention relates to a process for producing a bromo-aromatic condensed ring compound.

2. Description of the Related Art

Bromo-aromatic condensed ring compounds have been expected as raw substances for electronic conducting materials and intermediates for pharmaceutical products. For example, a process is disclosed for producing a poly-bromo compound, that is, 9,10-dibromoanthracene in 83 to 88% yield by brominating anthracene with bromine, in which the carbon number constituting the aromatic condensed ring is 14 (Organic Syntheses, vol. 1, pages 207–209).

When the process using bromine as a brominating agent is applied to an aromatic condensed ring compound in which the number of carbon atom constituting the aromatic condensed ring is 15 or more, however, it has been difficult to brominate said aromatic condensed ring compound. It has been also difficult to make the molar number of poly-bromo compounds in produced bromo-aromatic condensed ring compounds equal to or more than that of a mono-bromo compound.

The purpose of the present invention is to provide a convenient process for bromination of an aromatic condensed ring compound having 15 or more carbon atoms. The process also allows to make the molar number of poly-bromo compounds in produced bromo-aromatic condensed ring compounds equal to or more than that of a mono-bromo compound by brominating an aromatic condensed ring compound in which the number of carbon atom constituting the aromatic condensed ring is 15 or more.

SUMMARY OF THE INVENTION

The present invention relates to a process for producing a bromo-aromatic condensed ring compound which comprises reacting an aromatic condensed ring compound in which the number of carbon atom constituting the aromatic condensed ring is 15 or more with a N-bromo carboxylic acid amide in the presence of a chlorinated hydrocarbon compound and sulfuric acid to brominate said aromatic condensed ring compound.

DETAILED DESCRIPTION OF THE INVENTION

In the present invention, the aromatic condensed ring compound means a condensed polycyclic hydrocarbon in the form with the greatest number of non-neighboring double bonds or a heterocyclic compound in which one or more carbon atoms constituting said condensed polycyclic hydrocarbon are replaced by hetero atom(s). The condensed polycyclic hydrocarbons herein refer to condensed rings constituted by two or more independent rings that share only one side of the respective rings with each other [called "condensed"]. Said aromatic condensed ring compound may have a substituent such as an alkyl group, an alkenyl group, an aralkyl group, an aryl group, halogen or the like. Specific examples of these substituents include the same groups as specific examples for R described below.

Examples of the aromatic condensed ring compound in which the number of carbon atom constituting the aromatic condensed ring is 15 or more include pyrene, naphthacene, triphenylene, chrysene, picene, perylene, pentaphene, pentacene, hexaphene, hexacene, coronene, trinaphthylene, heptaphene, heptacene, pyranthrene, ovalene, aceanthrylene, acephenanthrylene, pleiadene, tetraphenylene, rubicene, coronene, phenanthridine and the like.

Amongst them, benzene condensed ring compound is preferred due to the facts that their bromination is relatively easy and that they are easily available as light-emitter materials. The benzene condensed ring compound herein includes compounds in which the condensed polycyclic hydrocarbons in the form with the greatest number of non-neighboring double bonds are constituted by benzene rings only. Examples thereof include pyrene, naphthacene, triphenylene, chrysene, picene, perylene, pentaphene, pentacene, hexaphene, hexacene, coronene, trinaphthylene, heptaphene, heptacene, pyranthrene and ovalene.

Amongst them, naphthacene compounds are preferred, rubrene compounds represented by the formula (1) shown below more preferred and compounds wherein n is zero are particularly preferred:

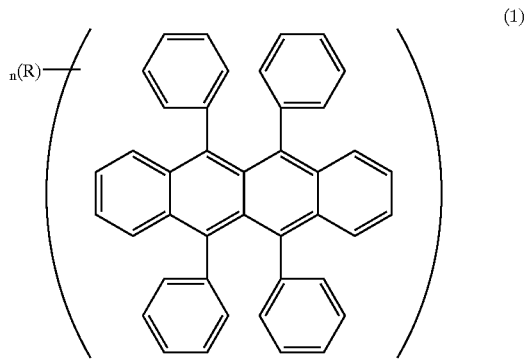

(1)

wherein R's each independently represent an alkyl group having 1 to 40 carbon atoms, an alkenyl group having 1 to 40 carbon atoms, an aralkyl group having 7 to 60 carbon atoms, an aryl group having 6 to 60 carbon atoms or halogen; and n represents an integer of 0 to 27. R's may further have a substituent.

In the formula (1) described above and the formula (2) described below, R's each independently include an alkyl group, an alkenyl group, an aralkyl group, an aryl group and halogen.

Examples of the alkyl group include methyl, ethyl, n-propyl, isopropyl, n-butyl, isobutyl, t-butyl, n-amyl, neopentyl, n-hexyl, cyclohexyl, n-octyl, n-nonyl, 2,3,4-trimethyl-3-pentyl, 2,4-dimethyl-3-pentyl and the like; and examples of the alkenyl group include 2-methyl-1-propenyl, 2-butenyl and the like.

Examples of the aralkyl group include benzyl, 2-phenylethyl, 2-naphthylethyl, diphenylmethyl and the like; and examples of the aryl group include phenyl, naphthyl, biphenyl and the like.

The above described alkyl, alkenyl, aralkyl, and aryl group may further have a substituent, for example, halogen such as fluorine, chlorine, bromine, and iodine; an alkoxy group such as methoxy, ethoxy, n-propoxy, t-butoxy and the like; an aryloxy group such as phenoxy and the like; a lower alkyl group such as methyl, ethyl, n-propyl, isopropyl, n-butyl, isobutyl, t-butyl, n-amyl, neopentyl, n-hexyl and the like; nitro; hydroxy and others.

The bromo-aromatic condensed ring compounds produced by the present invention are compounds in which one or more, preferably two or more, of hydrogen atoms in the above described aromatic condensed ring compounds are replaced by bromine and they may be a single substance or a mixture.

When a rubrene compound represented by the above formula (1), which is a benzene condensed ring compound, is used as the aromatic condensed ring compound, a bromorubrene compound represented by the formula (2) is obtained in the form of a single substance or a mixture.

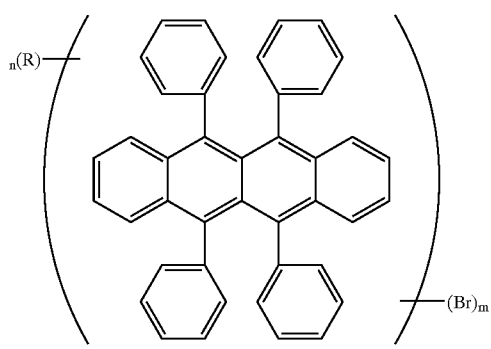

(2)

wherein R's each independently represent an alkyl group having 1 to 40 carbon atoms, an alkenyl group having 1 to 40 carbon atoms, an aralkyl group having 7 to 60 carbon atoms, an aryl group having 6 to 60 carbon atoms or halogen; m represents an teger of I to 28 and n represents an integer of 0 to 27, provided that the sum of m and n is 28 or less. R's may further have a substituent.

In the bromorubrene compound represented by the formula (2) described above, m is preferably 2 or more. On the other hand, m is preferably 20 or less, more preferably 10 or less and more preferably 5 or less. Amongst them, particularly preferred m is 2 or more and 5 or less.

As specific examples of bromorubrene compound represented by the formula (2), examples thereof are listed in Table 1 shown below, without being limited.

TABLE 1-continued

Compound (5) 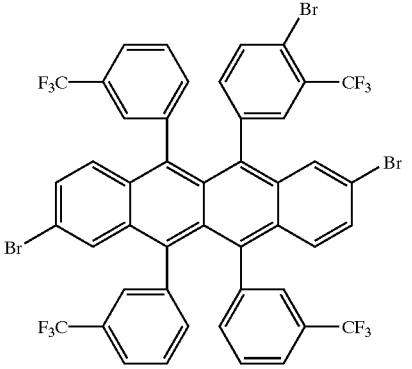

(6) 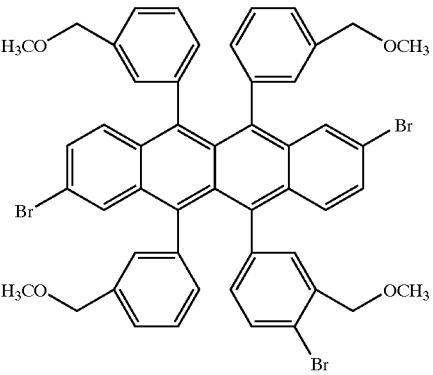

Examples of the N-bromocarboxylic acid amide used in the present invention include N-bromocarboxylic acid amides such as N-bromoacetamide, N-bromosuccinimide, N-bromophthalimide, isocyanuryl bromide, N-bromocaprolactam and the like. Among them, N-bromosuccinimide is preferable because it is widely used and easily available.

The amount of them to be used is varied depending on the bromo compound as desired and usually within a range of 1 mole to 10 moles, preferably 3 moles to 7 moles, per molar aromatic condensed ring compound as the raw material.

The chlorinated hydrocarbon compound used in the invention includes methylene chloride, chloroform, carbon tetrachloride, 1,2-dichloroethane and the like, with methylene chloride being preferred. The amount to be used is not particularly limited and usually 0.5 to 150 times, preferably 5 to 50 times of the aromatic condensed ring compound by weight.

Sulfuric acid to be used in the present invention is preferably a concentrated sulfuric acid. The concentrated sulfuric acid herein refers to sulfuric acid having a concentration of 90% or more, with a concentrated sulfuric acid having a concentration of about 97% being more preferred. The amount to be used is not particularly limited and usually 0.5 to 200 times, preferably 10 to 100 times of the aromatic condensed ring compound by weight.

In the process of the present invention, a substance other than the aromatic condensed ring compound, chlorinated hydrocarbon compound and sulfuric acid, for example, an organic solvent, an acid other than sulfuric acid or others can be used as far as the object of the invention is not injured.

Examples of the organic solvent usable in the present invention includes alcoholic solvents such as methanol, ethanol, isopropanol and the like; ether solvents such as ethyl ether, diethoxymethane, tetrahydrofuran, dimethoxyethane, dioxane and the like; saturated aliphatic hydrocarbon solvents such as hexane and the like; aromatic hydrocarbon solvents such as benzene, toluene, xylene and the like; amide solvents such as N,N-dimethylformamide, N-methylpyrrolidone, 1,3-dimethyl-2-imidazolidinone, N,N-dimethylacetamide and the like; ester solvents such as ethyl acetate, methyl acetate and the like.

The amount thereof to be used is not particularly limited and usually 0.5 to 200 times by weight of the aromatic condensed ring compound as used.

Examples of the acid other than sulfuric acid usable in the present invention include strong acids such as hydrochloric acid, hydrobromic acid, phosphoric acid, perchloric acid and the like.

The amount thereof to be used is not particularly limited and usually 0.5 to 200 times by weight of the aromatic condensed ring compound as used.

In the process of the present invention, the method of charging is not particularly limited. Usually, a conveniently used charging method is to mix an aromatic condensed ring compound with a chlorinated hydrocarbon compound, cool the mixture, add sulfuric acid to the mixture with agitation, stir the mixture to cause dissolution, and add N-bromosuccinimide.

In the process for production according to the invention, the reaction period is not particularly limited. Usually, the reaction is considered to be completed when substantially the whole of the aromatic condensed ring compound as the raw material is consumed. In other words, the reaction is usually completed between 0.5 hour and 24 hours.

In the the present invention, the reaction temperature is not particularly limited. Usually, it is preferred to ice-cool (to a reaction temperature of −5 to 5° C.) the mixture for 1 hour to 5 hours because heat production can be suppressed or side reaction can be controlled. Then, it is preferred to gradually elevate the temperature to room temperature (20° C.) and to stir at room temperature until the reaction is completed.

After completion of the reaction, the desired bromo-aromatic condensed ring compound can be obtained, for example, by pouring the reaction mixture into ice-water, extracting with an organic solvent such as toluene, ethyl acetate, diethyl ether, chloroform, dichloromethane or the like, washing the obtained organic layer with an aqueous sodium thiosulfate, washing with water and concentrating. Said compound can be purified, if necessary, by column chromatography, extraction, distillation or the like.

EXAMPLES

The invention will now be described in more detail with reference to Examples, which should not be considered to limit the present invention.

Example 1

After mixing 0.5 g (0.94 mmol) of rubrene with methylene chloride (10 g) and ice-cooling the mixture under stirring, 23 g of 97% sulfuric acid was added to the mixture. A solution was obtained by stirring the mixture to dissolution. To this solution was added 0.84 g (4.72 mmol) of N-bromosuccinimide. After completion of addition, the mixture was stirred under ice-cooling for 2.5 hours. Then, the temperature was gradually elevated to room temperature and the mixture was allowed to react for 2 hours with stirring. After completion of the reaction, the reaction solution was poured into 100 g of ice-water for dilution and extracted with chloroform. The organic layer was washed with an aqueous sodium thiosulfate and then with water. Said organic layer was dried over sodium sulfate, concentrated, evaporated by distilling the extraction solvent with an evaporator and purified by column chromatography (toluene/hexane) to give a mixture of bromorubrene compounds (0.45 g, yield: 62%). (The yield was calculated on the basis of the molecular weight of tribromorubrene.)

MS spectrum: $M^+$ 691.0, dibromorubrene; $M^+$ 768.9, tribromorubrene; $M^+$ 846.9, tetrabromorubrene; $M^+$ 926.7, pentabromorubrene.

The mixture of bromorubrene compounds was analyzed by liquid chromatography. When the sum of peak areas corresponding to mono-bromo compound and poly-bromo compounds was taken as 100%, the ratio of mono-bromo compound was 0% and the ratio of poly-bromo compounds was 100% (dibromo compound, 28.9%; tribromo compound, 7.3%; tetrabromo compound, 17.7%; pentabromo compound, 46.1%). Therefore, the mixture consisted substantially of poly-bromo compounds.

Comparative Example 1

After mixing 0.5 g (0.94 mmol) of rubrene with acetic acid (100 ml), one piece of iodine was added to the mixture under stirring. The mixture was stirred and 0.90 g (5.63 mmol) of bromine was added. After completion of addition, the temperature was elevated to 100° C. and stirred for 2 hours. Then, the mixture was gradually cooled to room temperature. After completion of the reaction, the reaction solution was poured into 100 g of ice-water for dilution and extracted with chloroform. The organic layer was washed with an aqueous sodium thiosulf ate and then with water. Said organic layer was dried over sodium sulfate, concentrated, evaporated by distilling the extraction solvent with an evaporator and purified by column chromatography (toluene/hexane) to give a mixture of bromorubrene compounds (0.44 g, yield: 68%). The yield was calculated on the basis of the molecular weight of dibromorubrene.

The mixture of bromorubrene compounds was analyzed by liquid chromatography. When the sum of peak areas corresponding to mono-bromo compound and poly-bromo compounds was taken as 100%, the ratio of mono-bromo compound was 62.7% and the ratio of poly-bromo compounds was 37.3% (dibromo compound, 35.5; tribromo compound, 1.8%). Therefore, the mixture contained more mono-bromo compound than poly-bromo compounds.

By applying the process of the present invention, bromination of an aromatic condensed ring compound having 15 or more carbon atoms can be conveniently conducted.

What is claimed is:

1. A process for producing a bromo-aromatic condensed ring compound which comprises reacting an aromatic condensed ring compound in which the number of carbon atom constituting the aromatic condensed ring is 15 or more with a N-bromo carboxylic acid amide in the presence of a chlorinated hydrocarbon compound and sulfuric acid to brominate said aromatic condensed ring compound.

2. The process for producing a bromo-aromatic condensedring compound according to claim 1, wherein the aromatic condensed ring compound is a benzene condensed ring compound.

3. The process for producing a bromo-aromatic condensed ring compound according to claim 2, wherein the benzene condensed ring compound is a rubrene compound represented by the formula (1):

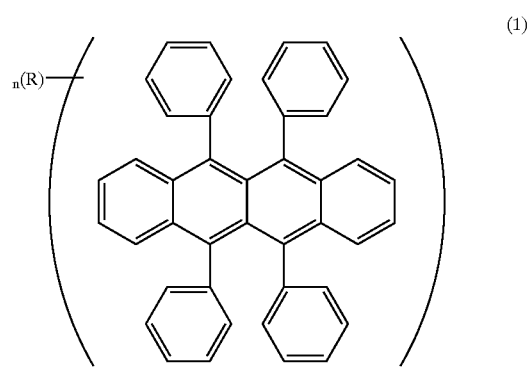

(1)

wherein R's each independently represent an alkyl group having 1 to 40 carbon atoms, an alkenyl group having 1 to 40 carbon atoms, an aralkyl group having 7 to 60 carbon atoms, an aryl group having 6 to 60 carbon atoms or halogen; and n represents integer of 0 to 27.

4. The process for producing a bromo-aromatic condensed ring compound according to claim 3, wherein the bromo-aromatic condensed ring compound is a bromorubrene compound represented the formula (2):

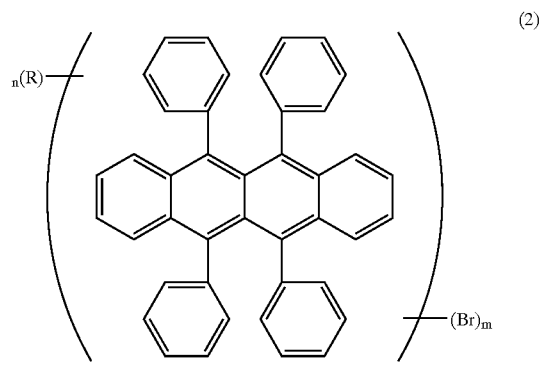

(2)

wherein R's each independently represent an alkyl group having 1to 40 carbon atoms, an alkenyl group having 1 to 40 carbon atoms, an aralkyl group having 7 to 60 carbon atoms, an aryl group having 6 to 60 carbon atoms or halogen; m represents an integer of 1 to 27 and n represents an integer of 0 to 27, provided that the sum of m and n is 28 or less.

* * * * *